(12) United States Patent
Pham et al.

(10) Patent No.: US 7,563,401 B2
(45) Date of Patent: Jul. 21, 2009

(54) TAMPON PLEDGET HAVING A SHAPED TIP AND METHOD OF MAKING SAME

(75) Inventors: Van T Pham, Dover, DE (US); Joseph S. Konrad, Dover, DE (US); Frederick N. Schaber, Smyrna, DE (US)

(73) Assignee: Playtex Products, Inc., Westport, CT (US)

( * ) Notice: Subject to any disclaimer, the term of this patent is extended or adjusted under 35 U.S.C. 154(b) by 0 days.

(21) Appl. No.: 10/876,981

(22) Filed: Jun. 25, 2004

(65) Prior Publication Data

US 2005/0022349 A1    Feb. 3, 2005

Related U.S. Application Data

(60) Provisional application No. 60/483,407, filed on Jun. 27, 2003.

(51) Int. Cl.
*B29C 31/08* (2006.01)
*B29C 35/16* (2006.01)
*B29C 57/10* (2006.01)
*A61F 13/20* (2006.01)

(52) U.S. Cl. ............... 264/320; 264/325; 28/118; 604/15

(58) Field of Classification Search ......... 264/299, 264/320, 324, 325; 604/14, 15, 904; 28/118, 28/120, 123, 124
See application file for complete search history.

(56) References Cited

U.S. PATENT DOCUMENTS

| | | | | |
|---|---|---|---|---|
| 2,416,706 A * | 3/1947 | McLaughlin | ............. | 28/118 |
| 2,849,000 A * | 8/1958 | Lewing | ............. | 604/368 |
| 3,821,350 A * | 6/1974 | Suchane | ............. | 264/257 |
| 3,866,737 A * | 2/1975 | Simon | ............. | 198/470.1 |
| 4,045,946 A * | 9/1977 | Schaefer | ............. | 53/550 |
| 4,302,174 A | 11/1981 | Hinzmann | ............. | 425/341 |
| 5,084,038 A | 1/1992 | Sheldon et al. | | |
| 5,433,912 A * | 7/1995 | Schulz et al. | ............. | 264/297.2 |
| 5,450,679 A * | 9/1995 | Mojden et al. | ............. | 34/105 |
| 5,788,910 A * | 8/1998 | McNelis et al. | ............. | 425/73 |
| 5,792,096 A | 8/1998 | Rentmeester et al. | ............. | 604/14 |
| 6,056,714 A | 5/2000 | McNelis et al. | | |
| 6,068,899 A | 5/2000 | Osborn, III et al. | ............. | 428/35.2 |
| 6,180,051 B1 * | 1/2001 | Schoelling | ............. | 264/443 |
| 6,432,075 B1 | 8/2002 | Wada et al. | ............. | 604/15 |
| 6,432,076 B1 | 8/2002 | Wada et al. | ............. | 604/15 |
| 6,478,764 B1 | 11/2002 | Suga | ............. | 604/15 |
| D485,354 S | 1/2004 | Carlin et al. | ............. | D24/125 |
| 2001/0018391 A1 | 8/2001 | Hull, Jr. et al. | ............. | 493/337 |

(Continued)

OTHER PUBLICATIONS

International Search Report dated May 12, 2005 corresponding to PCT International Application No. PCT/US04/20686.

*Primary Examiner*—Matthew J. Daniels
(74) *Attorney, Agent, or Firm*—Ohlandt, Greeley, Ruggiero & Perle, L.L.P

(57) ABSTRACT

The present invention provides a tampon pledget having a shaped tip. The present invention further provides a method for forming a tampon pledget having a shaped tip. The method includes a cooling step after the formation of the shaped tip, which results in the minimization and/or prevention of deformation of the shaped pledget tip during the remainder of processing up until the end use by a consumer.

15 Claims, 5 Drawing Sheets

U.S. PATENT DOCUMENTS

| | | | |
|---|---|---|---|
| 2002/0138035 A1 | 9/2002 | Hull, Jr. | 604/18 |
| 2003/0172504 A1 | 9/2003 | Sageser et al. | 28/118 |
| 2003/0176844 A1 | 9/2003 | Randall et al. | 604/385.17 |
| 2003/0176845 A1 | 9/2003 | Kollwitz et al. | 604/385.17 |

* cited by examiner

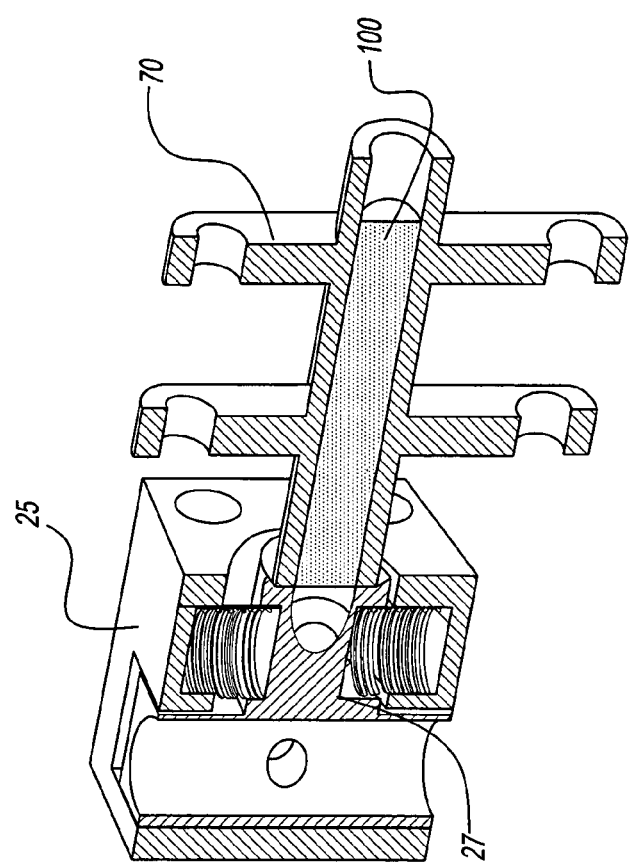
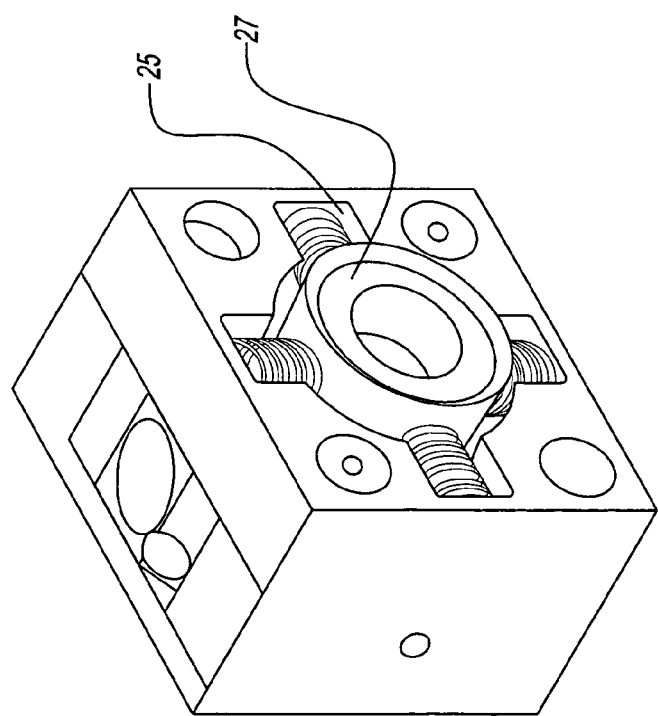

TAMPON PLEDGET HAVING A SHAPED TIP AND METHOD OF MAKING SAME

RELATED APPLICATION

This application claims priority to U.S. Provisional Patent Application Ser. No. 60/483,407 filed on Jun. 27, 2003.

BACKGROUND OF THE INVENTION

1. Field of the Invention

The present invention relates generally to a catamenial device or tampon pledget. More particularly, the present invention relates to a tampon pledget with a shaped insertion end or tip. The shaped end or tip resists deformation both during and after the formation process. The present invention also includes methods for making the shaped insertion end or tip.

2. Description of the Related Art

A catamenial insertion device normally has a pledget or tampon pledget and an applicator for insertion of the pledget. The applicator generally includes a tampon applicator barrel and a plunger. The plunger is adapted to telescopically slide in the barrel. The tampon pledget is an absorbent pledget that is positioned in the barrel. Generally, the barrel has an insertion end that has a tapered tip. The tapered tip normally is made with a plurality of petals. The petals cover a free or an insertion end of the pledget.

Generally, the pledget has a cylindrical shape. The pledget has a first or insertion end, and a second or string retaining end. The insertion end positioned adjacent an insertion end of the tampon applicator barrel may be flat or be tapered. A tapered shape is preferred. This tapered shaped facilitates insertion into the human body.

A problem in the art is that the shaped insertion end may be damaged during manufacture. The shaped insertion end or tip needs to maintain integrity during the formation process and after the formation process prior to use by the consumer. Such attempts to manufacture such a tip are often time consuming. These time consuming operations to form the shaped tip often are not conducive with high speed manufacturing of tampons at a high rate of speed. It has been observed that the method and apparatus for making such a shaped pledget tip also needs to be manufactured in a rapid manner in order to accommodate the manufacturing demands tampon pledgets.

Therefore, there is a need in the art for a shaped pledget insertion end or tip that can be processed in a rapid manner. There is also a need for a shaped pledget insertion end or tip that maintains its form or shape during the entire manufacture of the pledget, and at all other times prior to the end use by the consumer.

SUMMARY OF THE INVENTION

It is an object of the present invention to provide a tampon applicator pledget having a shaped insertion end or tip.

It is another object of the present invention to provide methods of making such tampon pledgets.

It is still another object of the present invention to provide a method for forming a tampon pledget having a shaped tip that includes a cooling step after the formation of the shaped tip.

It is a further object of the present invention to provide such a method for forming a tampon pledget having a shaped tip that includes forming the desired shape in a pledget forming device that is in a hot head drum, and then cooling the pledget immediately thereafter.

It is still a further object of the present invention to provide such a method for forming a plurality of tampon pledgets having a shaped tip that includes a device for locating and centering the shaped tip in order to form a symmetrically shaped tip.

It is yet a further object of the present invention to provide such a method for forming a tampon pledget having a shaped tip that provides a cooling step to minimize and/or prevent the shaped tip from deforming after formation and prior to use.

The above and other objects and advantages are provided by a process for manufacturing a pledget with a shaped tip according to the present invention. The process has a step of moving a plurality of absorbent members through a heating device with the absorbent members being connected to one another and each having a forward end and a rear end. The process also includes the step of heating the absorbent members. The heated absorbent members traverse through the heating device and are introduced to a first member having a first orifice therein with the orifice having a concave surface therein with an orifice end. The first member is movable in a plurality of directions for alignment with the heating device. The process further includes the step of pushing the plurality of heated absorbent members to the orifice end with the forward end of each forming a shaped tip. The formed pledgets are then cooled to set the shape and minimize and/or prevent deformation of the formed pledget during the remainder of the pledget processing and up to the use of the pledget by a consumer.

BRIEF DESCRIPTION OF THE DRAWINGS

FIG. 4 is an enlarged view of the hot head tool of FIGS. 1 and 3;

FIG. 5 is a cross-sectional view of the oven chain with an unformed pledget therein;

DETAILED DESCRIPTION OF THE INVENTION

Figure 1:
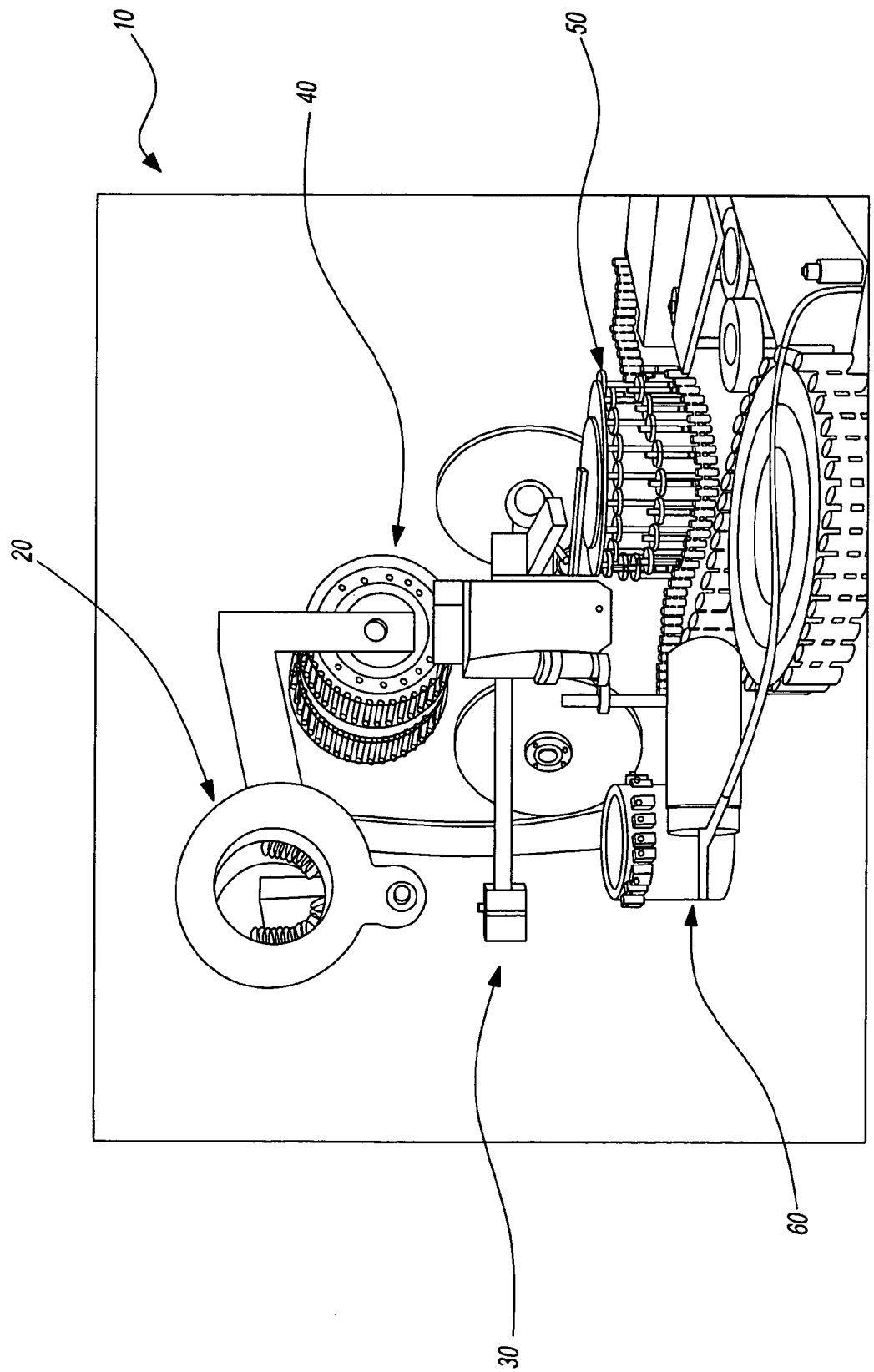
FIG. 1 is a perspective view of an apparatus and for making a shaped tampon pledget tip according to the present invention.
Figure 7:
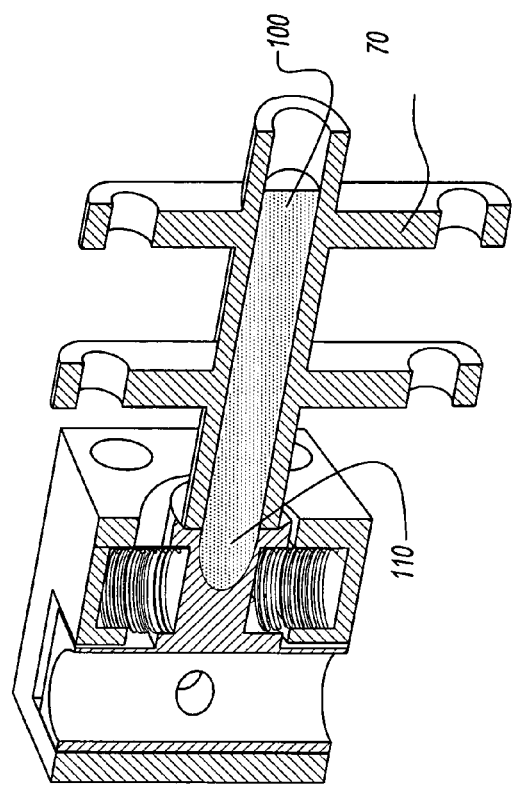
FIG. 7 is a cross-sectional view of the oven chain with a formed pledget having a shaped tip therein.

Referring to the drawings and, in particular, FIG. 1, there is shown a tampon apparatus or device generally represented by reference numeral 10. The tampon apparatus 10 is used to form pledget 100 having a shaped tip 110, as shown in FIG. 7. The tampon apparatus 10 is preferably a hot head tooling device for heating, shaping and crimping a suitable material for manufacturing a pledget having the shaped tip 110.

Figure 2:
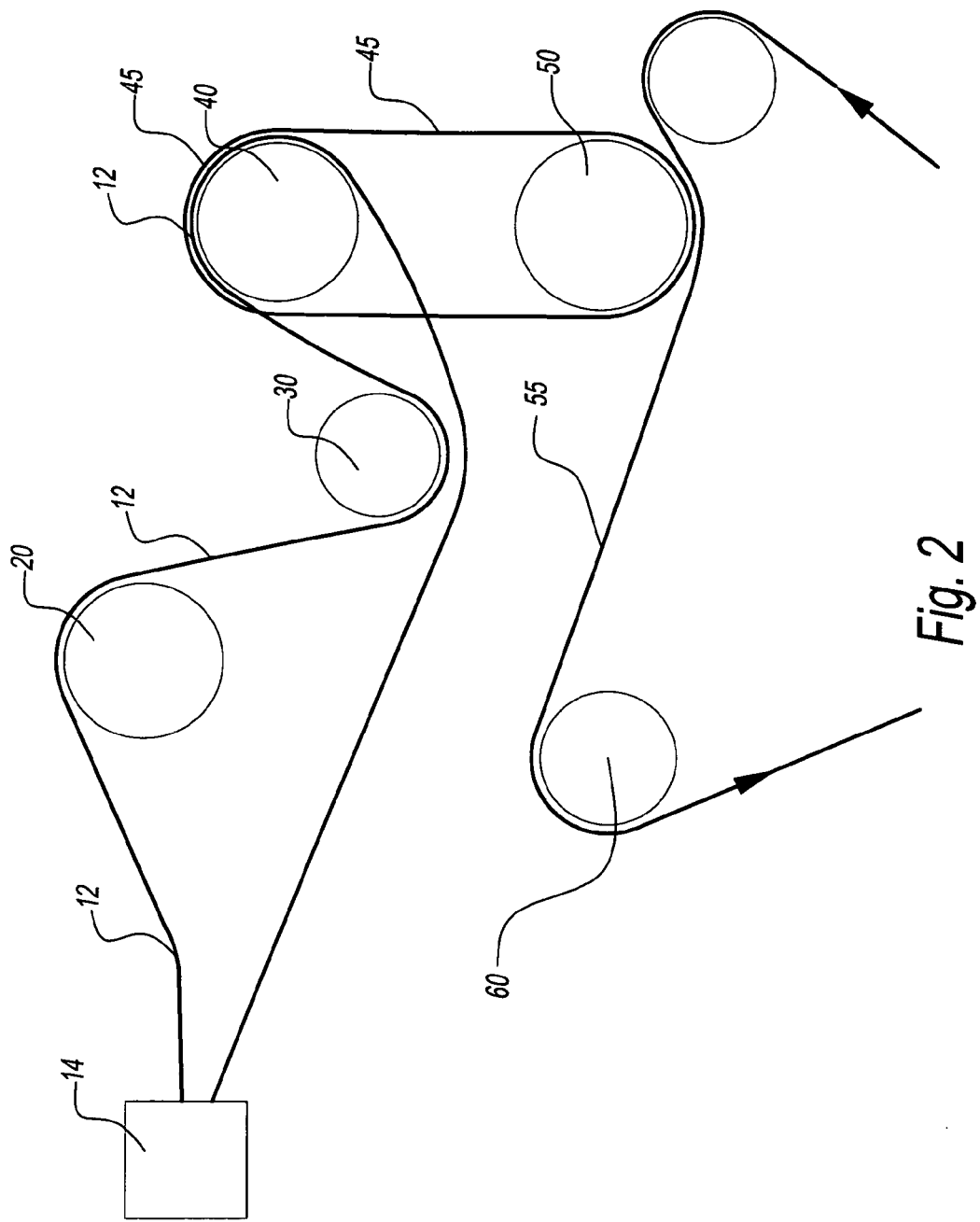
FIG. 2 is a schematic view of the apparatus of FIG. 1.

Referring to FIGS. 1 and 2, tampon apparatus 10 has a hot head drum 20 that receives an oven chain 12. The oven chain 12 is a number of the unformed pledgets being disposed in an arrangement from an oven 14 with one or more tampon pledgets 100 in an unformed state as shown in FIG. 5, thereon. The tampon pledget 100 is in a horizontal or virtually horizontal position. The oven chain 12 then moves the unformed tampon pledget 100 to a cooling area 30. After cooling, the oven chain 12 preferably further moves the tampon pledget 100 to a top transfer drum 40. The top transfer drum 40 is preferably an apparatus that receives tampon pledget 100.

The top transfer drum 40 preferably transfers the tampon pledget from the oven chain 12 to a transfer chain 45.

The transfer chain 45 moves tampon pledget 100 from the top transfer drum 40 to a bottom transfer drum 50. In this manner, an orientation of the unformed pledget 100 is changed. The orientation of the tampon pledget 100 is shifted preferably from a substantially horizontal or horizontal position to a substantially vertical position. The process further has the step of manipulating the tampon pledget 100 by a force. The force moves or pushes the tampon pledget 100 out of the transfer chain 45 by a push ram to a string chain 55. The string chain 55 preferably commences at a bottom most portion of the transfer drum 50.

The process further has a step of moving the tampon pledget 100 by a string chain 55 to a pre-punch drum 60. The pre-punch drum 60 is preferably a device that is connected to a tampon forming machine. The tampon forming machine may be any device known in the art for forming a conventional packaged tampon for consumer usage. The pre-punch drum 60 preferably pre-punches the unformed pledget 100 to form a string-receiving hole. The hole preferably facilitates easier insertion of a string into the tampon pledget. Thereafter, the tampon pledget 100 is placed in an applicator barrel. Various applicator barrels can be placed therearound as are known in the art.

The oven chain 12 thus moves from oven 14 about the sides and upper surface of hot head drum 20, through cooling area 30, about the sides and upper portion of top transfer drum 40 and back to hot head drum 20. The transfer chain 45 moves, preferably in a continuous manner, about top transfer drum 40 and bottom transfer drum 50. The string chain 55 moves from bottom transfer drum 50 to pre-punch drum 60 and after other movement back to the bottom transfer drum.

Figure 3:
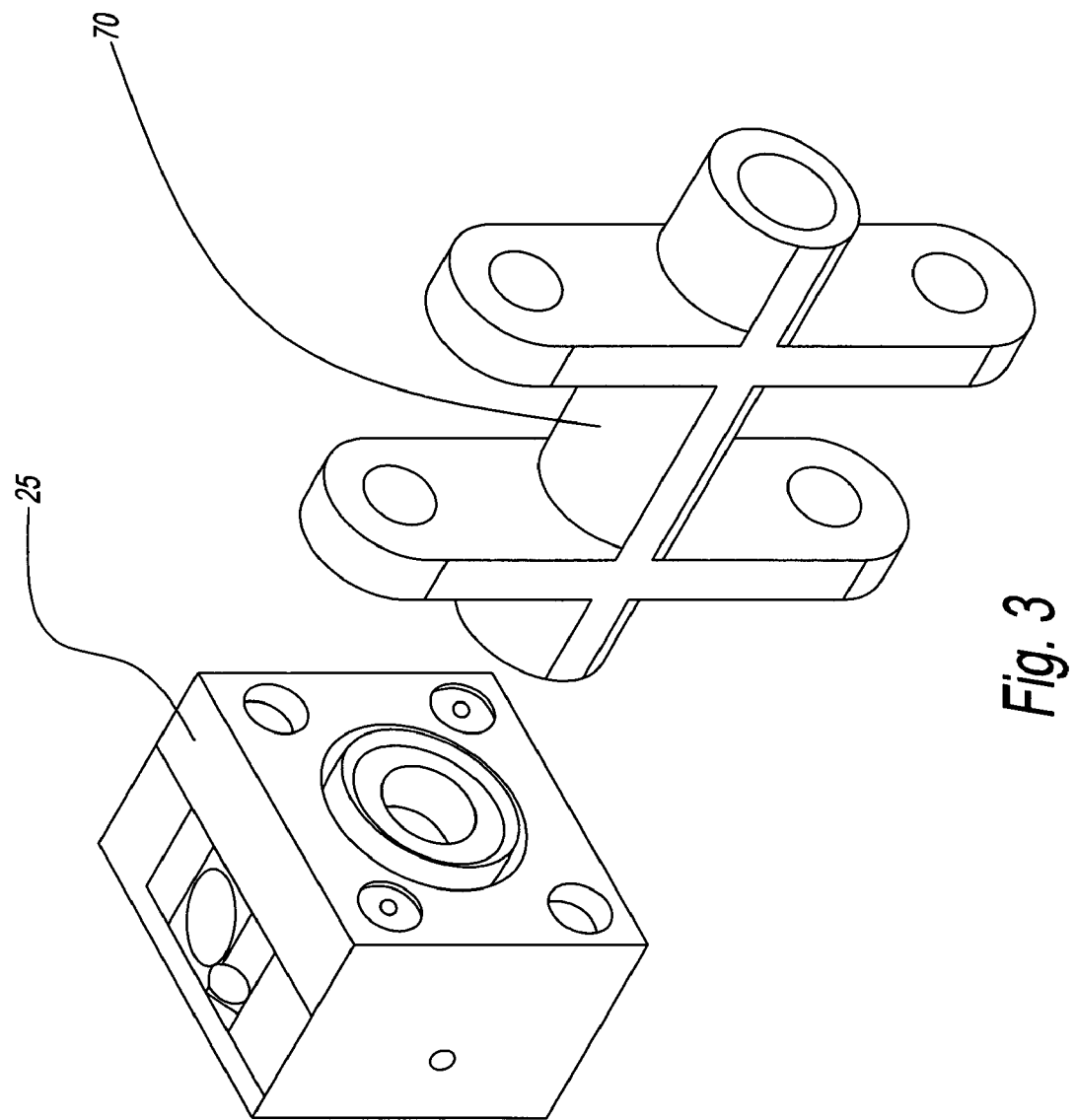
FIG. 3 is an enlarged, schematic view of a hot head tool and oven chain of the apparatus of FIG. 1.
Figure 6:
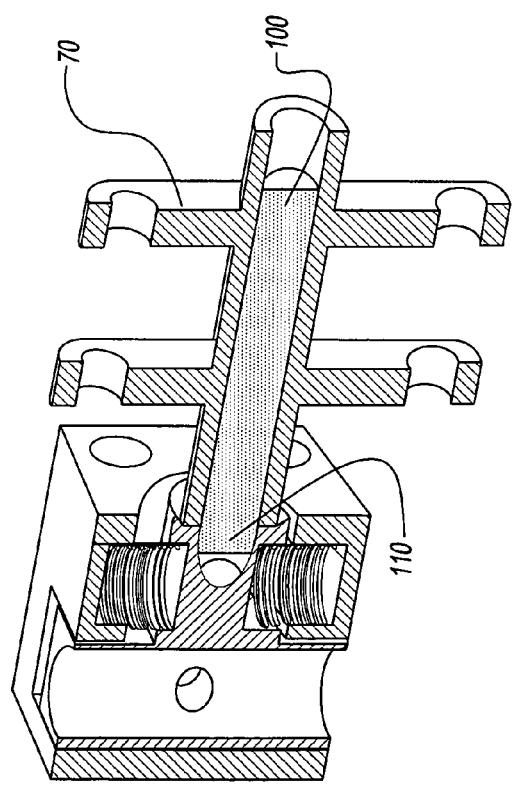
FIG. 6 is a cross-sectional view of the oven chain with a pledget having a partially formed shaped tip therein.

The oven chain 12 travels around hot head drum 20 with the pledget 100 from the oven 14 formed thereon as a cylinder with both ends in a blunt or flat condition. The hot head drum 20 of tampon apparatus 10 has one or more, preferably between about 18 to about 36, and more preferably about 28, hot head assemblies 25. Each hot head assembly 25 has a hot head tool 27 shown in FIGS. 3 and 4. These hot head tools 27 are positioned about the outer circumference or surface of hot head drum 20. At hot head drum 20, tampon pledget 100 is pushed into oven chain 12, as shown in FIG. 5, by any conventional means, such as a push ram, until tip end 110 of pledget 100 is completely in hot head tool 25 as shown in FIG. 7. The pledget 100 is moved from the position shown in FIG. 5 to the position shown in FIG. 7 in about 0.8 seconds. The pledget 100 is in the position shown in FIG. 7 for about 1.2 seconds. Thus, the formation of shaped tip 110, namely from FIG. 5 to FIG. 7 takes about 2 seconds.

The hot head tool 27 in hot head assembly 25 acts to create the shape of shaped or formed pledget tip 110. The hot head tool 27 can be designed with any depth and any profile or taper thereby forming the desired shape of shaped tip 110. In a preferred embodiment of the present invention, the hot head tool 27 is designed to provide a tapered tip. The hot head tool may also be formed from a thermally conductive material.

Referring to FIG. 4, hot head assembly 25 has hot head tool 27 as a part thereof. The hot head tool 27 has the ability to move back and forth along the three axial directions, namely the X, Y and Z axes. This ability to move in three axes provides for the alignment of the tool with the oven chain 14. When oven chain 14 is aligned or centered to hot head tool 27, it will allow pledget 100 to be concentric to hot head tool 27 to create a consistent shape to shaped or formed tip 110. The hot head tool may be aligned in an automatically, manually, or a combination thereof. Automatic alignment may be facilitated by the use of a microprocessor.

The oven temperature of the oven in the oven chain 14 is adjusted to achieve a bonding temperature of the pledget tip and may be in a range between about 200° F. to about 305° F. depending on the size of the pledget. Preferably, the oven temperature of the oven in the oven chain 14 is in a range between about 230° F. to about 250° F. depending on a size of the pledget.

In a critical aspect of the present invention, the oven chain 14 with pledget 100 having shaped tip 110 is introduced to cooling area 30. The shaped tip 110 is exposed to a reduced temperature atmosphere at cooling area 30. While any appropriate cooling method or means may be employed to cool the shaped pledget, there are three preferred methods that can be used to cool shaped tip 110 according to the present invention. It has been unexpectedly found that the heating then cooling of the shaped tip 110 imparts hardness to the pledget that results in the shaped pledget maintaining its shape and resisting deformation. This is beneficial for efficiently manufacturing and handling of the pledgets.

It has been found that cooling the shaped pledget at a temperature between about 30° F. to about 60° F. achieves the desired effect. Preferably, the shaped pledget is cooled at a temperature between about 50° F. to about 60° F., and more preferably about 56° F.

In a first embodiment of the present invention, the cooling method includes converting filtered compressed air (air filtered compressed air to medical grade of compressed air) into cool air. Cool air is introduced or delivered in the direction of movement of oven chain 14. The cool air is emitted by any manner known in the art. Most preferably, the cool air is emitted by at least one, preferably two, and possibly more than two, nozzles.

The at least one nozzle emits cool air for between about 0.5 seconds to about 2 seconds. Preferably the cool air is emitted for between about 0.5 seconds to about 1 second, on tampon pledget 100.

In a second embodiment, the cooling method includes the use of a chiller or chiller chamber or tunnel and fan to create the desired cool air environment. One skilled in the art should appreciate that the chiller may be any device known in the art for cooling air or gas such as by use of a refrigerant or any other manner known in the art. In this method, the air is cooled, and thus tampon pledget 100, at the desired temperature. This method avoids the use of compressed air. In this embodiment, tampon pledget 100 is cooled for about 0.5 seconds to about 2 seconds, and more preferably for about 0.5 seconds to about 1 second.

In a third embodiment of the present invention, the cooling method includes applying a cool surface to the shaped pledget. Suitable surfaces that may be cooled include, but are not limited to, an inner surface of a first head tool member, any surface of a first orifice, or any combinations thereof. Suitable materials for forming the cooling surfaces include, but are not limited to, stainless steel, other metallic-based material, or any other thermally conductive material. The cool surface is maintained at the desired temperature, such as those temperatures described above. Again, with this cooling method as well, tampon pledget 100 is cooled for about 0.5 seconds to about 2 seconds, and more preferably about 0.5 seconds to about 1 second.

The cooling of shaped tip 110 hardens or sets the shaped or formed pledget tip 110 and minimizes and/or prevents the shaped tip from deformation during the transfer process from oven chain 12 to transfer chain 45. Thus, cooling of shaped tip 110 immediately after formation by the use of cooling area 30 provides for shaped or formed tip 110 to retaining its shape during the transfer process. Furthermore, the use of hot head tool 27 in hot head drum 20 provides for concentric positioning of oven chain 12 and tampon pledget 100, and thus shaped tip 110 during formation, and thereby the creation of a consistent, concentric shaped or formed tip.

The apparatus 10 makes on an average between about 350 to about 600 pledgets per minute, and preferably between about 300 to about 500 pledgets per minute with each pledget having a shaped tip 110. More preferably, about 400 pledgets per minute on average can easily be made with apparatus 10. One skilled in the art should appreciate that each pledget is easier to manipulate and that more pledgets with the shaped tip 110 will be manufactured in an undamaged state and this method increases productivity.

Pledget 100 can be made of rayon including multi-lobed rayon, cotton, or any combinations thereof. Pledget 100 can have a coverstock. The coverstock can be made of polyester, or polyester coated with polyethylene. Preferably, the pledget 100 is made of rayon or a combination of rayon and multi-lobed rayon. Also, preferably, pledget 100 has a coverstock that is made of polyester coated with polyethylene.

The present invention has been described with particular reference to the preferred forms thereof. It will be obvious to one of ordinary skill in the art that changes and modifications may be made therein without departing from the spirit and scope of the present invention.

What is claimed is:

1. A process for manufacturing a pledget, the process comprising:
    moving an absorbent member through a heating device, said absorbent member having a forward end and a rear end;
    heating said absorbent member;
    introducing said absorbent member to a first member having an orifice therein, said orifice having a concave surface therein with an orifice end;
    pushing said heated absorbent member to said orifice end, said forward end of said heated absorbent member forming a shaped tip; and
    cooling said heated absorbent member using a cooling device,
    wherein said first member moves in a first lateral direction, a second longitudinal direction, and a third direction being substantially perpendicular to both said first lateral and said second longitudinal direction.

2. The process of claim 1, wherein said first member is a head tooling die.

3. The process of claim 1, wherein the cooling device provides a cooled air stream, and wherein the cooling step further comprises the step of blowing said cooled air stream on said heated absorbent member to cool said shaped tip.

4. The process of claim 1, wherein the cooling device provides a cooled surface, and wherein the cooling step further comprises the step of contacting said shaped tip with said cooled surface to cool said shaped tip.

5. The process of claim 1, wherein the cooling step includes a fan, wherein said fan blows a cooled gaseous substance on said shaped tip through a plurality of nozzles.

6. The process of claim 1, wherein said shaped tip is substantially tapered.

7. The process of claim 1, wherein said cooling step hardens said shaped tip for preventing a deformation therefrom.

8. The process of claim 1, wherein said cooling step is conducted at a temperature between about 30° F. to about 60° F.

9. The process of claim 1, wherein the cooling step is conducted for a time between about 0.5 seconds to about 2 seconds.

10. The process of claim 1, wherein said heating device is an oven operating at a temperature between about 200° F. to about 305° F.

11. A process for manufacturing a pledget, the process comprising:
    moving a plurality of absorbent members through an oven in a chain, said plurality of absorbent members being connected to one another, each of said plurality of absorbent members having a forward end and a rear end;
    heating said plurality of absorbent members in said oven;
    introducing said plurality of heated absorbent members to a movable first head tooling member having an orifice therein, said orifice having a depth and a concave surface therein with an orifice end;
    moving said plurality of heated absorbent members in said orifice end using an insertion force, said forward end of each of said plurality of heated absorbent members forming a shaped tip, wherein said plurality of heated absorbent members are introduced through said orifice in substantially a centered fashion; and
    cooling said plurality of heated absorbent members using a cooling device to form the pledget,
    wherein said movable first head tooling member moves in a first direction, a second direction being perpendicular to said first direction, and a third direction being perpendicular to both said first direction and said second direction, said first through third directions being capable of moving said movable first head tooling member and aligning said movable first head tooling member with said oven.

12. The process of claim 11, wherein the cooling step includes a cooled air stream, and further comprises the step of blowing said cooled air stream on said plurality of heated absorbent members to cool said shaped tip.

13. The process of claim 11, wherein the cooling step includes a cooled surface, and further comprises the step of contacting said shaped tip with said cooled surface, thereby cooling said shaped tip.

14. The process of claim 11, wherein the cooling step is provided by blowing a cooled gaseous substance on said shaped tip through a plurality of nozzles.

15. The process of claim 13, wherein said cooled surface is selected from the group consisting of an inner surface of said movable first head tooling member, said first orifice, a lateral side of said first orifice, said concave surface, said orifice end, and any combinations thereof.

* * * * *